United States Patent [19]

Slinkard

[11] 4,146,734

[45] Mar. 27, 1979

[54] OXIDATION OF BUTENE TO ACETIC ACID AND CATALYST THEREFOR

[75] Inventor: William E. Slinkard, Corpus Christi, Tex.

[73] Assignee: Celanese Corporation, New York, N.Y.

[21] Appl. No.: 822,581

[22] Filed: Aug. 8, 1977

[51] Int. Cl.² .................... C07C 51/32; B01J 23/10; B01J 23/22; B01J 23/06
[52] U.S. Cl. .................................. 562/548; 252/462; 252/464
[58] Field of Search ............................ 252/462, 464; 260/533 R

[56] References Cited

U.S. PATENT DOCUMENTS 3,900,428  8/1975  Mai et al. ............................. 252/462

FOREIGN PATENT DOCUMENTS 45-31165  10/1970  Japan.

OTHER PUBLICATIONS

Galasso, "Structure, Properties and Preparation of Perovskite-Type Compounds", Pergamon Press, 1969, pp. 20-22.

Primary Examiner—W. J. Shine
Attorney, Agent, or Firm—Stewart N. Rice; Ralph M. Pritchett

[57] ABSTRACT

A butene may be oxidized in the vapor phase at elevated temperatures to produce acetic acid by reacting the butene with molecular oxygen in the presence of a catalyst comprising a composition of the empirical formula:

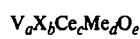

$$V_a X_b Ce_c Me_d O_e$$

wherein V is vanadium, Ce is cerium, and O ix oxygen, wherein X represents a metal which is one or more of Y, La, Pr, Nd, Sm, Eu, Gd, Dy and Yb, and wherein Me represents a metal which is one or more of Bi, Ti, Zn and Sn or mixtures thereof, Ce and Me being optionally present.

25 Claims, No Drawings

OXIDATION OF BUTENE TO ACETIC ACID AND CATALYST THEREFOR

BACKGROUND OF THE INVENTION

The present invention relates to a method for the vapor phase oxidation of a butene to produce acetic acid and to catalysts therefor.

Numerous catalysts, especially vanadium-containing catalysts, are known in the prior art for the oxidation of a butene to produce acetic acid. Among those disclosed in the prior art are mixed oxides of vanadium and titanium, tin, aluminum, or antimony as disclosed in U.S. Pat. No. 3,917,682 issued Nov. 4, 1975 to Tetsuo Mizukami, et al. Japanese Pat. No. 45-31165 published Oct. 8, 1970 discloses butene oxidation catalysts comprising mixed oxides of vanadium and cerium or cadmium, and wherein phosphorous, boron or arsenic may optionally be present. U.S. Pat. No. 3,704,317 issued Nov. 28, 1972 to Takashi Yamashita, et. al, discloses a catalyst whose effective elements are vanadium and one or more elements selected from the group consisting of lithium, boron, silicon, chromium, iron, nickel, zinc, zirconium, niobium, ruthenium, rhodium, palladium, tantalum and bismuth. German Offenlegungsschrift No. 2,041,073 discloses mixed oxide catalysts wherein there is present vanadium plus at least one of antimony and titanium, and at least one of tin, iron, manganese, nickel or copper, and optionally molybdenum and/or tungsten. German Offenlegungsschrift No. 2,354,425 discloses that a mixed oxide of vanadium and zinc is an effective catalyst, and that a mixed oxide of vanadium and zirconium is an effective catalyst, and also discloses various other metal oxide catalysts.

French Pat. No. 2,092,544 discloses a mixed oxide catalyst containing vanadium and one or more of tin, antimony, titanium and aluminum. Chemical Abstracts, Vol. 74, Pages 316-317, Note 41924a, discloses that Japanese Pat. 79-30,802 discloses that mixed oxide catalysts containing vanadium together with iron, nickel or cobalt, and optionally, in addition, phosphorous, boron or arsenic, are useful for butene oxidation. In addition to the foregoing, there are numerous other prior art references to the use of mixed oxides of vanadium with one or more other various metals and to the methods of preparing such catalysts.

Since there has been a great amount of research into suitable catalysts for the vapor phase oxidation of butene to acetic acid, particularly vanadium-containing catalysts, the prior art catalysts give relatively good results. However, in view of the importance of the process and in view of the fact that even small increases in efficiency will make a big difference in the economics of a process, research is constantly under way in order to find new and better catalysts for the vapor phase oxidation of a butene, alone or in mixture with other butenes, to produce acetic acid.

It is thus an object of the present invention to provide a new and useful process for the vapor phase oxidation of butenes to acetic acid. It is another object of the present invention to provide a unique catalyst composition for such purposes. A still further object of the present invention is to provide a process, and catalyst therefor, for the vapor phase oxidation of butenes to acetic acid which provide improved selectivity. Additional objects of the present invention will be apparent from the following description.

SUMMARY OF THE INVENTION

These and other objects are accomplished by the present invention, which in one of its aspects is a process for the production of acetic acid by vapor phase oxidation of a butene comprising reacting, in the vapor phase and at elevated temperatures, said butene with molecular oxygen in the presence of a catalyst comprising a composition of the empirical formula:

$$V_a X_b Ce_c Me_d O_e$$

in which formula V is vanadium, O is oxygen, Ce is cerium, X is at least one member selected from the group consisting of yttrium, lanthanum, praseodymium, neodymium, samarium, europium, gadolinium, dysprosium and ytterbium, and Me is at least one member selected from the group consisting of bismuth, titanium, zinc and tin, and wherein the atomic ratio of the elements in said composition is such that, when a is 10, b is from about 1 to 11, c is from 0 to 9, d is from 0 to about 15, e is a number of at least 20 such that the valence requirements of V, X, Ce and Me are satisfied, and the sum of b, c and d does not exceed about 20. If X represents two or more elements, then b represents the total numbers of those elements. Likewise, if Me represents two or more elements, then d represents the total numbers of those elements. In another one of its aspects, the present invention is the foregoing catalyst.

DETAILED DESCRIPTION OF THE INVENTION

The novelty of the present invention resides in the above mentioned unique catalyst composition. It has been found that the catalyst gives very good selectivity to acetic acid. Acetaldehyde is also a significant product, this being important since acetaldehyde can be further oxidized to acetic acid. The general range of atomic ratios of the elements in the catalyst composition are set forth above. A very good catalyst results when the number of atoms of the rare earth metal or metals represented by X are equal to or greater than the number of atoms of cerium, if any, which are present, that is that b be equal to or greater than c in the above formula. The presence of cerium is not required in the catalyst although good results are obtained with cerium present. In the foregoing formula, vanadium atoms should represent at least about one-third or more of catalyst metal atoms present; and, thus in general, when a is 10, the sum of b, c and d should not exceed about 20. Preferably, when a is 10, the sum of b, c and d is from about 5 to 15. Also, when a is 10, preferably the sum of b and c is at least about half of d. Me, which represents one or more of bismuth, titanium, zinc, or tin, serves as a promoter. Although a promoter metal represented by Me does not have to be present in the catalyst, it has been found that the addition of bismuth, titanium, zinc and/or tin may raise the selectivity by 5% to 10%. Preferably the promoter is present in such an amount that, when a is 10, d is from about 5 to 10. The exact structures of the catalysts of the present invention are not known, but they may be considered as a mixture of the oxides of the various metals and/or as mixed metal oxides and/or as a vanadate.

All of the rare earth metals represented by X in the foregoing formula provide good results. Preferred particular catalyst compositions are those of the empirical formulas $VSmO_e$, $VDyO_e$, $V_2PrO_e$, $V_2GdO_e$ and $V_6Nd_3Zn_2O_e$. In all such formulas, e is a number which will satisfy the valence requirements of the metals present. The especially preferred catalyst is one of the empirical formula $V_2LnO_e$ wherein Ln represents a mixture or rare earth metals derived from a mixed rare earth metal salt of the Lanthanide series which salt will provide 65% by weight of rare earth oxides upon calcining, the remaining 35% being ignition products such as water of hydration, carbon oxides and the like, with the mixture of rare earth oxides obtained therefrom being about 34% $La_2O_3$, 13% $Nd_2O_3$, 48% $CeO_2$, 4% $Pr_6O_{11}$ and 1% other rare earth oxides.

The catalysts of the present invention may be prepared by various procedures known in the art for these type catalysts. A good method of preparation is a joint precipitation method wherein there is first formed a hydrochloric acid solution of a vanadium oxide, salt or hydroxide and an oxide, salt or hydroxide of the other metal or metals to the present in the catalyst. This solution is then neutralized by the addition of base, preferably ammonia, to obtain a precipitate which is separated from the mother liquor and then washed, dried at 50° to 150° C., preferably 80° to 120° C., and calcined at 350° to 600° C., preferably 400° to 550° C. In neutralizing the hydrochloric acid solution, preferably the base and the hydrochloric acid solution are simultaneously poured into a container of water so as to maintain pH within the range of about 6 to 7. After the calcined catalyst is obtained, it may be granulated to the desired size. If a shaped catalyst is desired, the shaping is advantageously accomplished by shaping the calcined, granulated catalyst, although the wet precipitate might be shaped before drying and calcining operations take place. In some cases it may be advantageous to treat the catalyst so obtained by treating it with aqueous hydrochloric acid, washing with water, drying and re-calcining.

As pointed out above, in forming the hydrochloric acid solution the source of the catalyst metal may be an oxide, a hydroxide or a salt. All of these generally provide equally good results. If salts are used as the metal source, the carbonates, nitrates, acetates and chlorides are preferred. Mixed rare earth carbonates, chlorides and nitrates are commercially available, and these may be suitably used.

Another good preparative technique is an evaporation method wherein an aqueous solution of an ammonium vanadate, such as $NH_4VO_3$, or vanadyl oxalate, is combined with an aqueous solution of a salt (such as a nitrate or acetate) of the other metal or metals, and then solidified by evaporation. The recovered solid is dried and calcined as above. Other preparative techniques may also be employed. For example, the catalyst may be prepared by heating and calcining under proper conditions a slurried mixture of the oxides of the various metals.

The catalyst may be used with or without a chemically inactive carrier or support, although particularly good results are obtained with unsupported catalysts. Suitable chemically inactive supports include alumina, silica, pumice, diatomaceous earth, titanium dioxide, carborundum and silicon carbide. Loading of the catalyst onto a desired support may be accomplished by conventional techniques. For example, the catalyst can conveniently be deposited on the support by carrying out the precipitation in the presence of the support, but the catalyst may also be combined with the support after the precipitate has been washed.

In carrying out the butene oxidation process, the catalyst may be in any form which is suitable for fluidized, moving or fixed bed operation. The size and configuration of the catalyst grains are not critical, but depend on whether the catalyst is used in a fixed, moving or fluidized bed. The contact time of the reactants with the catalyst at the reaction conditions should generally be between about 0.1 and 60 seconds, but is preferably a contact time within the range of about 1 to 10 seconds. As used herein the term contact time refers to the contact time adjusted to 25° C. and atmospheric pressure (conditions denoted by NTP). The contact time is calculated by dividing the volume of the catalyst bed, including voids, by the volume per unit time flow rate of the reactants at NTP.

The oxidation of the butene may be carried out continuously or noncontinuously. The temperature utilized in the vapor phase oxidation process should generally be within the range of about 180° to 400° C., preferably within the range of 200° to 350° C. The pressure utilized in the vapor phase oxidation may be subatmospheric, atmospheric, or superatmospheric and generally should be within the range of about 1 to 30 atmospheres absolute, preferably within the range of about 1 to 20 atmospheres absolute. The temperature selected will depend somewhat on the contact time and reactor configuration being used. Conversion is a function of temperature, and variations in temperature will cause variations in conversion. Thus, within limits, butene conversion will increase with increases in temperature, however, selectivity tends to decrease with increasing temperatures and increasing conversions. Thus the choice of a particular temperature involves a balancing of the desired conversion against the desired selectivity.

The oxygen necessary as a reactant in the vapor phase oxidation may be from concentrated molecular oxygen or may be from a more dilute oxygen-containing gas wherein the molecular oxygen is mixed in varying amounts with an inert diluent gas such as nitrogen, argon or carbon oxides. Air is preferably used as the source of oxygen. The butene and the oxygen-containing gas should be premixed before entering the reaction zone. The contact of the butene and the oxygen-containing gas are, however, preferably kept to a minimum before entering the reaction zone. The reactants may be pretreated before entering the reaction zone such as for the removal of undesirable components therefrom.

In conducting the oxidation reaction, the gaseous feed mixture should generally contain from about 1 to 20, preferably 2 to 10, moles of oxygen per mole of butene. Although it is not required, water vapor or steam is also desirably present in the gaseous feed in amounts of from about 1 to 50, preferably 5 to 30, moles of water per mole of butene. Some combinations of the ranges disclosed herein will be within explosive limits. Care should be taken to operate outside the explosive range. The presence of water vapor will aid in temperature control during the reaction, which is exothermic in nature, and will also serve to increase selectivity of the reaction to acetic acid. Care should be taken to avoid contacting the catalyst with liquid water during operation. In addition to water, diluents which are gaseous under the reaction conditions and are relatively inert may be introduced into the system. Suitable diluents include carbon dioxide, nitrogen, and flue gas as well as paraffinic hydrocarbons such as are frequently present in commercially available butene. Any of the butenes are suitable for the vapor phase oxidation of the present invention, and the invention may be applied to oxidize a feed made up of a single butene or mixtures of butenes. Specifically, the present invention may be used for the vapor phase oxidation of butene-1, cis-butene-2, trans-butene-2 and isobutene, or mixtures of any two or more of these butenes. Saturated butenes may be present in the butene feedstock without affecting the oxidation reaction, but the reactivity of butanes is low.

In the oxidation of butenes, the hydrocarbon chain is cleaved and a terminal carbon is oxidized to form an acid. The oxidation of the n-butenes results in the highest yields of acetic acid and/or acetaldehyde which can be oxidized to acetic acid; with some propionic acid being formed. Oxidation of isobutene, as compared to the n-butenes, results in less favorable yields of acetic acid and/or acetaldehyde. The gaseous reaction product recovered from the vapor phase oxidation will generally contain not only the desired acetic acid and substantial amounts of acetaldehyde, but also some hydrocarbons, carbon monoxide, carbon dioxide, oxygen, steam, propionic acid, maleic acid, formic acid, acetone, formaldehyde and other lower carbonyl compounds.

The gaseous reaction product recovered from the vapor phase oxidation may be treated by conventional condensation and fractional distillation techniques to recover the acetic acid product. Acetaldehyde may be recovered and further oxidized. In some cases it may be advantageous to recycle unreacted gases to the reactor. By cooling the gaseous reaction product to condense the acetic acid, a crude aqueous acid solution with an acetic acid concentration of about 10% to 50% by weight may be obtained. Concentration and recovery of acetic acid from the dilute crude aqueous solution may be performed by solvent extraction and subsequent distillation, or by other conventional techniques.

As used herein the term "conversion" means mole percent conversion, and is calculated by multiplying the moles of butene converted times 100 and dividing such by the moles of butene fed. As used herein the term "selectivity" of a particular product means mole percent selectivity, and is calculated by multiplying the number of carbon atoms in the moles of the particular product obtained times 100, and dividing such by the number of carbon atoms in the moles of all products recovered.

The following examples are given to illustrate the invention but are not to be interpreted as limiting the scope thereof.

CATALYST A 18.2 grams of vanadium pentoxide ($V_2O_5$) and 30.3 grams of yttrium trichloride ($YCl_3$) are dissolved in 300 milliliters of concentrated hydrochloric acid and 300 milliliters of water. The acid solution is then added dropwise with stirring to 300 milliliters of water while simultaneously adding concentrated ammonium hydroxide to maintain the pH at about 6–7. Ice bath cooling is employed to keep the temperature below 30° C. After the addition is complete, the reaction mixture is stirred an additional hour. The resulting precipitate is collected on a filter, washed thoroughly with water, dried at 100° C., and then calcined at 500° C. for about 16 hours. After calcining, the catalyst is comminutated to provide a granulated catalyst material of a $-20+30$ mesh size of the empirical formula $V_2YO_e$.

CATALYST B

Using the procedure for preparation of Catalyst A, a catalyst of the empirical formula $VDyO_e$ is prepared from 9.1 g vanadium pentoxide, 30.1 g $DyCl_3.6H_2O$ and 8.7 g $Dy(NO_3)_3.5H_2O$.

CATALYST C

Using the procedure for preparation of Catalyst A, a catalyst of the empirical formula $V_2PrO_e$ is prepared from 18.2 g vanadium pentoxide and 35.5 g $PrCl_3.6H_2O$.

CATALYST D

Using the procedure for preparation of Catalyst A, a catalyst of the empirical formula $V_2GdO_e$ is prepared from 12.2 g vanadium pentoxide and 25.0 g $CdCl_3.6H_2O$.

CATALYST E

Using the procedure for preparation of Catalyst A, a catalyst of the empirical formula $V_2YbO_e$ is prepared from 18.2 g vanadium pentoxide and 38.7 g $YbCl_3.6H_2O$.

CATALYST F

Using the procedure for preparation of Catalyst A, except that calcining time is 5 hours, a catalyst of the empirical formula $V_4SmO_e$ is prepared from 36.4 g vanadium pentoxide and 36.4 g $SmCl_3.6H_2O$.

CATALYST G

Using the procedure for preparation of Catalyst A, except that calcining time is 7 hours, a catalyst of the empirical formula $V_2EuO_3$ is prepared from 12.5 g vanadium pentoxide and 25.0 g $EuCl_3.6H_2O$.

CATALYST H

Using the procedure for preparation of Catalyst A, except that calcining time is 7.5 hours, a catalyst of the empirical formula $V_2NdO_e$ is prepared from 18.2 g vanadium pentoxide and 35.8 g $NdCl_3.6H_2O$.

CATALYST I 18.2 grams of vanadium pentoxide ($V_2O_5$) and 51.2 g samarium chloride are dissolved in 400 milliliters of concentrated hydrochloric acid, and then about 500 milliliters of water are added. The acid solution is then neutralized to a pH of about 6–7 by addition of concentrated ammonium hydroxide. The resulting brown precipitate is collected on a filter, washed thoroughly with water, dried at 100° C., and then calcined at 500° C. for about 16 hours. After calcining, the catalyst is comminutated to provide a granular catalyst material of a $-20+30$ mesh size of the empirical formula $VSmO_e$.

CATALYST J 18.2 grams of vanadium pentoxide ($V_2O_5$) and 74.2 grams of lanthanum trichloride ($LaCl_3$) are dissolved in 400 milliliters of concentrated hydrochloric acid. The acid solution is then added dropwise with stirring to 300 milliliters of water while simultaneously adding concentrated ammonium hydroxide to maintain the pH at about 6–7. After the addition is complete, the reaction mixture is stirred an additional hour. The resulting precipitate is collected on a filter, washed thoroughly with water and then calcined at 500° C. for about 5 hours to obtain a catalyst of the empirical formula $VLaO_e$. 37.5 grams of the calcined catalyst is then slurried with 41 grams of an ammonia stabilized silica sol carrier and the water removed by a rotary evaporator. The resulting solids are calcined at 400° C. for about 3 hours to yield a supported catalyst containing about 25% by weight of silica.

CATALYST K 36.4 grams of vanadium pentoxide is dissolved in 300 milliliters of concentrated hydrochloric acid. To this solution is added slowly in small portions 53.2 g of a mixed rare earth carbonate which will provide about 65% by weight of rare earth oxides upon calcining, the distribution of the rare earth oxides obtained therefrom being by weight, 66% $La_2O_3$, 24% $Nd_2O_3$, 0.7% $CeO_2$, 8.2% $Pr_6O_{11}$ and 1.1% other rare earth oxides. After addition is complete, the reaction mixture is stirred and heated until all the solid has dissolved, then cooled to ambient temperature, and then added dropwise with stirring to 300 milliliters of water. Concentrated ammonium hydroxide is added at the same time to maintain the pH within the range of about 6–7. After addition is complete, the reaction mixture is stirred for an additional hour and the precipitate collected on a filter. The precipitate is washed with water, dried at 110° C. and calcined at 500° C. for about 7.5 hours to obtain a catalyst of the empirical formula $V_2LnO_e$ wherein Ln is a mixture of rare earth metals of the Lanthanide series in the ratios derived from the rare earth carbonate as specified above.

CATALYST L

A catalyst is formed in accordance with the procedure of Catalyst K except that a mixed rare earth carbonate is utilized which, upon calcining, will provide about 65% by weight of rare earth oxides of the Lanthanide series with the distribution of the rare earth oxides obtained therefrom being, by weight, 60.0% $La_2O_3$, 21.5% $Nd_2O_3$, 10.0% $CeO_2$, 7.5% $Pr_6O_{11}$ and 1.0% other rare earth oxides. The atomic ratio of vanadium ions to rare earth metal ions was 2:1.

CATALYST M

A catalyst is formed in accordance with the procedure of Catalyst K except that a mixed rare earth carbonate is utilized which, upon calcining, will provide about 65% by weight of rare earth oxides of the Lanthanide series with the distribution of the rate earth oxides obtained therefrom being, by weight, 34.0% $La_2O_3$, 13.0% $Nd_2O_3$, 48.0% $CeO_2$, 4.0% $Pr_6O_{11}$ and 1.0% other rare earth oxides. The atomic ratio of vanadium ions to rare earth metal ions was 2:1.

CATALYST N

Using the procedure for preparation of Catalyst A, a catalyst of the empirical formula $V_6Nd_3Zn_2O_e$ was prepared from 27.3 g vanadium pentoxide, 53.5 g $NdCl_3.6H_2O$ and 13.6 g $ZnCl_2$.

CATALYST O

Using the procedure for preparation of Catalyst A, a catalyst of the empirical formula $V_2PrBiO_e$ is prepared from 18.2 g vanadium pentoxide, 35.5 g $PrCl_3.6H_2O$ and 48.5 g $Bi(NO_3)_3.5H_2O$.

CATALYST P

Using the procedure for preparation of Catalyst A, a catalyst of the empirical formula $V_2GdSnO_e$ is prepared from 36.4 g vanadium pentoxide, 74.2 g $GdCl_3.6H_2O$ and 70.2 g $SnCl_4.5H_2O$.

CATALYST Q

Using the procedure for preparation of Catalyst A, except that calcining time is 7.5 hours, a catalyst of the empirical formula $V_2NdTiO_e$ is prepared from 18.2 g vanadium pentoxide, 35.8 g $NdCl_3.6H_2O$ and 19 g $TiCl_4$.

OXIDATION EXAMPLES

Several runs are made wherein the above prepared catalysts are used in the vapor phase oxidation of butenes to acetic acid. In each of the runs a U-shaped stainless steel tube is employed to hold the catalyst charge. The tube is about 61 centimeters tall with the catalyst containing section having an inside diameter of about 12 millimeters. The usual catalyst charge is about 5cc of $-20+30$ mesh material physically mixed with 5cc of 24 grit silicon carbide. The catalyst is placed in the down flow leg of the reactor and supported on a stainless steel screen. The reactor is heated to the desired temperature using a molten salt bath. Flow rates of the butene and air reactants are determined, and corrected to 0° C. and atmospheric pressure (STP), with a soap-film bubble meter. Water at a known flow rate is flashed to steam with the flow rate of steam calculated by application of the ideal gas law. After the desired feed rates of butene, air and steam are established, the combined feed gas is passed over the catalyst and the temperature of the salt bath adjusted to obtain the desired butene conversion level. After steady state conditions are achieved, material balances are then obtained. All the runs are conducted at or near atmospheric pressure. The reaction products plus unreacted butenes, if any, oxygen, nitrogen and steam are passed through a condenser after leaving the heated reaction zone to remove the liquid products and water from the vent stream. The vent stream, now containing primarily unreacted butenes, if any, carbon oxides, nitrogen, oxygen, plus some uncondensed acetaldehyde and acetone, are analyzed continuously using standard gas chromatographic techniques. The liquid product is collected after the end of the experiment and its composition determined also by standard gas chromatographic techniques.

Reaction conditions and results of each of the runs are listed in Table I. All flow rates are corrected to STP. In all of the runs a mixture of 1-butene (32% by volume), 2-butene (17% by volume) and isobutene (51% by volume) is oxidized.

TABLE I

| Catalyst | Reactor Temp. ° C | Feed Rate, cc/min | | | Butene Conversion, Mole % | Selectivity, Mole % | |
|---|---|---|---|---|---|---|---|
| | | Air | Steam | Butene | | Acetic Acid | Acetaldehyde |
| A | 279 | 144 | 62.1 | 3.88 | 87.4 | 30.3 | 8.8 |
| B | 273 | 142 | 59.2 | 4.11 | 82.7 | 30.3 | 10.5 |
| C | 282 | 144 | 66.8 | 4.19 | 90.0 | 30.1 | 10.3 |

TABLE I-continued

| Catalyst | Reactor Temp. °C | Feed Rate, cc/min | | | Butene Conversion, Mole % | Selectivity, Mole % | |
|---|---|---|---|---|---|---|---|
| | | Air | Steam | Butene | | Acetic Acid | Acetaldehyde |
| D | 290 | 132 | 58.0 | 3.75 | 93.3 | 31.5 | 9.6 |
| E | 278 | 138 | 60.4 | 3.80 | 91.7 | 31.1 | 8.8 |
| F | 248 | 135 | 49.8 | 3.46 | 97.8 | 23.4 | 8.9 |
| G | 279 | 137 | 62.5 | 4.04 | 87.1 | 29.4 | 10.3 |
| H | 284 | 133 | 68.9 | 4.14 | 94.0 | 29.5 | 8.4 |
| I | 278 | 126 | 53.2 | 2.77 | 95.5 | 30.4 | 11.6 |
| J | 331 | 203 | 97.2 | 5.05 | 90.3 | 27.2 | 8.4 |
| K | 281 | 142 | 116.0 | 5.80 | 93.7 | 31.2 | 10.2 |
| L | 279 | 109 | 88.9 | 4.41 | 98.0 | 33.7 | 6.7 |
| M | 274 | 106 | 86.2 | 4.31 | 98.0 | 33.6 | 10.5 |
| N | 289 | 117 | 92.0 | 4.50 | 99.8 | 32.4 | 8.4 |
| O | 280 | 140 | 66.2 | 4.20 | 90.5 | 32.1 | 11.4 |
| P | 298 | 135 | 60.0 | 3.88 | 93.0 | 33.5 | 11.0 |
| Q | 280 | 137 | 71.0 | 4.20 | 93.5 | 30.8 | 10.2 |

The embodiments of the invention in which an exclusive property or privilege is claimed are defined as follows:

1. A process for the production of acetic acid by vapor phase oxidation of a butene comprising reacting, in the vapor phase and at elevated temperatures within the range of about 180° to 400° C., said butene with molecular oxygen in the presence of a catalyst comprising a composition of the empirical formula:

$$V_a X_b Ce_c Me_d O_e$$

in which formula V is vanadium, O is oxygen, Ce is cerium, X is at least one member selected from the group consisting of yttrium, lanthanum, praseodymium, neodymium, samarium, europium, gadolinium, dysprosium and ytterbium, Me is at least one member selected from the group consisting of bismuth, titanium, zinc and tin, and wherein the atomic ratio of the elements in said composition is such that when a is 10, b is from about 1 to 11, c is from 0 to about 9, d is from 5 to about 10 e is a number of at least 20 such that the valence requirements of V, X, Ce and Me are satisfied, the sum of b, c, and d is from about 5 to 15, and the sum of b and c is at least half the number represented by d.

2. The process of claim 1 wherein b is equal to or greater than c.

3. The process of claim 1 wherein c is 0.

4. The process of claim 1 wherein said process is conducted at a pressure within the range of about 1 to 20 atmospheres absolute, wherein water vapor is present in amounts of from about 1 to 50 moles per mole of said butene, and wherein oxygen is present in amounts of from about 1 to 20 moles per mole of said butene.

5. The process of claim 2 wherein at least half of the atoms of metal represented by X are yttrium atoms.

6. The process of claim 2 wherein at least half of the atoms of metal represented by X are lanthanum atoms.

7. The process of claim 2 wherein at least half of the atoms of metal represented by X are praseodymium atoms.

8. The process of claim 2 wherein at least half of the atoms of metal represented by X are neodymium atoms.

9. The process of claim 2 wherein at least half of the atoms of metal represented by X are samarium atoms.

10. The process of claim 2 wherein at least half of the atoms of metal represented by X are europium atoms.

11. The process of claim 2 wherein at least half of the atoms of metal represented by X are gadolinium atoms.

12. The process of claim 2 wherein at least half of the atoms of metal represented by X are dysprosium atoms.

13. The process of claim 2 wherein at least half of the atoms of metal represented by X are ytterbium atoms.

14. A catalyst comprising a composition of the empirical formula:

$$V_a X_b Ce_c Me_d O_e$$

in which formula V is vanadium, O is oxygen, Ce is cerium, X is at least one member selected from the group consisting of yttrium, lanthanum, praseodymium, neodymium, samarium europium, gadolinium, dysprosium and ytterbium, Me is at least one member selected from the group consisting of bismuth, titanium, zinc and tin, and wherein the atomic ratio of the elements in said composition is such that when a is 10, b is from about 1 to 11, c is from 0 to about 9, d is from 5 to about 10, e is a number of at least 20 such that the valence requirements of V, X, Ce and Me are satisfied,
the sum of b, c and d is from about 5 to 15, and the sum of b and c is at least half the number represented by d.

15. The catalyst of claim 14 wherein c is 0.

16. The catalyst of claim 14 wherein b is equal to or greater than c.

17. The catalyst of claim 16 wherein at least half the atoms represented by X are yttrium atoms.

18. The catalyst of claim 16 wherein at least half the atoms represented by X are lanthanum atoms.

19. The catalyst of claim 16 wherein at least half the atoms represented by X are praseodymium atoms.

20. The catalyst of claim 16 wherein at least half the atoms represented by X are neodymium atoms.

21. The catalyst of claim 16 wherein at least half the atoms represented by X are samarium atoms.

22. The catalyst of claim 16 wherein at least half the atoms represented by X are europium atoms.

23. The catalyst of claim 16 wherein at least half the atoms represented by X are gadolinium atoms.

24. The catalyst of claim 16 wherein at least half the atoms represented by X are dysprosium atoms.

25. The catalyst of claim 16 wherein at least half the atoms represented by X are ytterbium atoms.

* * * * *

UNITED STATES PATENT AND TRADEMARK OFFICE
CERTIFICATE OF CORRECTION

PATENT NO. : 4,146,734
DATED : March 27, 1979
INVENTOR(S) : William E. Slinkard

It is certified that error appears in the above—identified patent and that said Letters Patent are hereby corrected as shown below:

In column 6, line 18, change "$Cd\ Cl_3 \cdot 6H_2O$" to -- $Gd\ Cl_3 \cdot 6H_2O$ --.

Signed and Sealed this

Twenty-sixth Day of June 1979

[SEAL]

Attest:

RUTH C. MASON
*Attesting Officer*

DONALD W. BANNER
*Commissioner of Patents and Trademarks*